(12) United States Patent
Hussein et al.

(10) Patent No.: US 11,857,691 B2
(45) Date of Patent: Jan. 2, 2024

(54) AUTONOMOUS DISINFECTANT SYSTEM

(71) Applicant: SABAN VENTURES PTY LIMITED, Lane Cove (AU)

(72) Inventors: Mahdi Elsayed Hussein, Lane Cove (AU); Madeleine Jane Clegg, Lane Cove (AU); Brian Hingley, Lane Cove (AU); Ronald Peter Weinberger, Lane Cove (AU)

(73) Assignee: SABAN VENTURES PTY LIMITED, Lane Cove (AU)

( * ) Notice: Subject to any disclaimer, the term of this patent is extended or adjusted under 35 U.S.C. 154(b) by 611 days.

(21) Appl. No.: 16/096,680

(22) PCT Filed: Apr. 28, 2017

(86) PCT No.: PCT/AU2017/050387
§ 371 (c)(1),
(2) Date: Oct. 25, 2018

(87) PCT Pub. No.: WO2017/185138
PCT Pub. Date: Nov. 2, 2017

(65) Prior Publication Data
US 2020/0147249 A1    May 14, 2020

(30) Foreign Application Priority Data
Apr. 29, 2016  (AU) ............................... 2016901582

(51) Int. Cl.
*A61L 2/24*   (2006.01)
*A61L 2/10*   (2006.01)
*A61L 2/16*   (2006.01)

(52) U.S. Cl.
CPC .................. *A61L 2/24* (2013.01); *A61L 2/10* (2013.01); *A61L 2/16* (2013.01); *A61L 2202/14* (2013.01)

(58) Field of Classification Search
CPC ..... A61L 2/24; A61L 2/10; A61L 2/16; A61L 2202/14
See application file for complete search history.

(56) References Cited

U.S. PATENT DOCUMENTS 7,692,172 B2   4/2010   Leben
8,097,861 B2   1/2012   Leben
(Continued)

FOREIGN PATENT DOCUMENTS

KR    20120062050 A      6/2012
WO    WO2006/070281 A2   7/2006
(Continued)

OTHER PUBLICATIONS

Office Action issued in corresponding Chinese Application No. 201780026605.X (including English-language translation) (24 pages).
(Continued)

*Primary Examiner* — Sean E Conley
(74) *Attorney, Agent, or Firm* — MH2 TECHNOLOGY LAW GROUP LLP

(57) ABSTRACT

Described herein is a disinfectant system in the form of an autonomous device for performing a disinfectant operation within an enclosed space defined by the walls, ceiling and floor of a room when a predefined condition, in the form of the absence of a human being within the room, is met. The purpose of the system is environmental decontamination and specifically to inactivate pathogenic organisms. The device includes a disinfectant module for carrying out the disinfectant operation when there is an absence of a human being within the room, and a sensing module for sensing the presence of a substantially stationary human being within the room.

19 Claims, 7 Drawing Sheets

(56) References Cited

U.S. PATENT DOCUMENTS

| | | | |
|---|---|---|---|
| 8,859,994 B2 | 10/2014 | Deal | |
| 9,517,284 B1* | 12/2016 | Stibich | A61L 2/10 |
| 2002/0085947 A1 | 7/2002 | Deal | |
| 2003/0201909 A1* | 10/2003 | Hilliard | G08G 1/02 |
| | | | 340/940 |
| 2006/0107670 A1* | 5/2006 | Thomle | F24F 11/0001 |
| | | | 62/129 |
| 2008/0243273 A1* | 10/2008 | Robert | A61L 9/12 |
| | | | 700/67 |
| 2009/0005650 A1* | 1/2009 | Angell | G16H 50/30 |
| | | | 600/300 |
| 2011/0191950 A1* | 8/2011 | Liu | A47K 13/305 |
| | | | 4/233 |
| 2012/0266920 A1* | 10/2012 | Burt | E03D 9/005 |
| | | | 134/24 |
| 2012/0305787 A1 | 12/2012 | Henson | |
| 2014/0044590 A1 | 2/2014 | Trapani | |
| 2015/0258234 A1* | 9/2015 | Larsen | A61L 2/202 |
| | | | 422/4 |
| 2016/0220716 A1* | 8/2016 | Childress | B64D 11/02 |
| 2017/0049915 A1* | 2/2017 | Brais | A61L 9/20 |
| 2023/0110384 A1 | 4/2023 | Lloyd | |

FOREIGN PATENT DOCUMENTS

| | | |
|---|---|---|
| WO | 2009/097389 A1 | 8/2009 |
| WO | 2013/116566 A1 | 8/2013 |
| WO | 2015/030840 A1 | 3/2015 |
| WO | 2016/209632 A1 | 12/2016 |

OTHER PUBLICATIONS

International Search Report and Written Opinion dated May 29, 2017 in corresponding International Application No. PCT/AU2017/050387, 10 pages.

Extended European Search Report dated Mar. 30, 2020 in corresponding European Application No. 17788432.7, 21 pages.

Examination Report No. 1 dated Oct. 28, 2020 in corresponding Australian Application No. 2017256814, 4 pages.

Office Action issued in corresponding Chinese Application No. 201780026605.X dated Feb. 23, 2021 (including English-language translation) (20 pages).

Office Action issued in corresponding Australian Application No. 2017256814 dated Jul. 6, 2021 (3 pages).

Office Action issued in corresponding Chinese Application No. 201780026605.X dated Sep. 3, 2021 (including English-language translation) (14 pages).

* cited by examiner

AUTONOMOUS DISINFECTANT SYSTEM

CROSS-REFERENCE TO RELATED APPLICATION(S)

This application is a national stage entry from International Application No. PCT/AU2017/050387, filed on Apr. 28, 2017, and claims priority from Australian Patent Application No. 2016901582, filed on Apr. 29, 2016, the entire contents of all of which are incorporated herein by reference.

FIELD OF THE INVENTION

The present invention relates to an autonomous disinfectant system for performing a disinfectant operation within an enclosed space under a predefined condition. Embodiments of the invention have been particularly developed for use in hospital rooms to carry out a disinfectant operation at any time when a room is clear of any human presence. While some embodiments will be described herein with particular reference to that application, it will be appreciated that the invention is not limited to such a field of use, and is applicable in broader contexts

BACKGROUND

Any discussion of the background art throughout the specification should in no way be considered as an admission that such art is widely known or forms part of common general knowledge in the field.

Hospital acquired infections (HAIs) are an increasing problem in hospitals and medical clinics. Around 200,000 people are infected by HAIs in Australia each year, about 7000 of which are fatal. Sick patients inevitably spread germs in the air and across many surfaces which can then easily be picked up by staff, visitors or other patients, particularly those with depressed immune systems. Furthermore staff, patients or visitors can also act as carriers and transfer bacteria between rooms.

To minimize HAIs and the spread of HAIs, surfaces and rooms in general must be decontaminated. Entire room decontamination often involves applying chemical disinfectants to surfaces via the manual use of spray bottles and wipes. However, near impossible to guarantee the adequate disinfection of each and every surface which could be harbouring pathogenic germs using these manual methods.

In recent years, several technologies for whole room decontamination have arisen. One such technology is the use of Ultra Violet (UV) radiation. UV radiation occupies the part of the electromagnetic spectrum just below visible light (shorter wavelengths). UV radiation is germicidal as photons of this frequency carry enough energy to damage cell structures and DNA.

Current UV decontamination products are used to assist with terminal disinfection, which is a room disinfection occurring when a room is vacant, that is, after a patient has been checked out of a room and ceases to be a source of infection. Recent studies have shown that these UV utilizing processes lead to a general decrease in HAIs when used to assist terminal disinfection.

Known UV decontamination products are movable, manually operated units. Such devices are physically moved and positioned in an empty room by an operator and manually activated when the room is unoccupied and all access points are closed. These devices have shown to reduce HAIs when used to assist in terminal disinfection.

However, the known manually operated UV decontamination devices are difficult and time consuming to set up, run and monitor. The nature of their design requires significant labour, time and effort from their operators to deploy safely and effectively. Furthermore, these units are generally relatively large, bulky and heavy which provides difficulties for transporting the units and storing the units.

Furthermore, due to the general nature of manual operation, the known manually operated UV decontamination devices are prone to human error and provide no clear, foolproof instructions for ensuring the system has been deployed correctly each time. The manual nature of the known devices creates additional work for personnel and, additionally, can interfere with the work flow of other duties.

Finally, many known UV decontamination devices are single point emission sources. Therefore, such devices may not suitably disinfect many shadowed areas throughout a space as these areas do not receive an adequate UV dose to inactivate germs on such surfaces. Alternatively, such devices may need to be repositioned several times in order to decontaminate the majority of the space.

SUMMARY OF THE INVENTION

It is an object of the present invention to overcome or ameliorate at least one of the disadvantages of the prior art, or to provide a useful alternative.

In accordance with a first aspect of the present invention there is provided a disinfectant system for performing a disinfectant operation within an enclosed space when a predefined condition is met, the system including:
  a disinfectant module for carrying out the disinfectant operation when the predefined condition is met; and
  a sensing module including at least one sensor for sensing the presence of all substantially stationary and/or an intermittently mobile humans or animals within the enclosed space;
  wherein the predefined condition is the absence of any human or animal within the enclosed space.

In an embodiment, the sensing module includes a plurality of sensors. In a further embodiment, at least one of the plurality of sensors is operatively associated with one another. In another embodiment, each of the plurality of sensors are operatively associated with one another.

In an embodiment, the sensing module includes at least one energy emission detecting sensor. In an embodiment, the at least one energy emission detecting sensor is used to identify shape and form of the human or animal.

In an embodiment, the at least one energy emission detecting sensor includes an imaging sensor. In an embodiment, the imaging sensor is a long wavelength infrared sensor.

In an embodiment, the at least one energy emission detecting sensor is used to identify macro-movement of the human or animal. In an embodiment, the at least one energy emission detecting sensor includes a passive infrared (PIR) sensor.

In an embodiment, the at least one energy emission detecting sensor is used to identify sound from the presence of the human or animal. In an embodiment, the at least one energy emission detecting sensor includes at least one microphone. In further embodiments, the at least one energy emission detecting sensor includes array of microphones.

In an embodiment, the at least one energy emission detecting sensor is used to identify vibration from the presence of the human or animal. In an embodiment, the at least one energy emission detecting sensor includes at least one an accelerometer.

In an embodiment, the at least one energy emission detecting sensor is used to identify a temperature change caused by the presence of the human or animal. In an embodiment, the at least one energy emission detecting sensor includes at least one temperature sensor. In a further embodiment, the at least one temperature sensor is a thermometer.

In an embodiment, the sensing module includes at least one energy reflection, shadowing, transmission or absorption detecting sensor that detects energy reflection, shadowing, transmission or absorption.

In an embodiment, the at least one energy reflection, shadowing, transmission or absorption detecting sensor is used to identify shape and form of the human or animal. In an embodiment, the at least one energy reflection, shadowing, transmission or absorption detecting sensor includes at least one imaging sensor. In a further embodiment, the at least one imaging sensor is a visible light or short wavelength infrared camera. In another embodiment, the at least one energy reflection, shadowing, transmission or absorption detecting sensor includes at least one radar sensor.

In an embodiment, the at least one energy reflection, shadowing, transmission or absorption detecting sensor is used to identify macro-movement of the human or animal. In an embodiment, the at least one energy reflection, shadowing, transmission or absorption detecting sensor includes a ranging sensor. In a further embodiment, the ranging sensor is one of the group containing: a ranging radar sensor, an ultrasonic sensor or a laser sensor.

In an embodiment, the at least one energy reflection, shadowing, transmission or absorption detecting sensor is used to identify micro-movement of the human or animal. In an embodiment, the at least one energy reflection, shadowing, transmission or absorption detecting sensor includes a Doppler sensor. In a further embodiment, the Doppler sensor is one of the group containing: a Doppler radar sensor, an ultrasonic sensor or a laser sensor.

In an embodiment, the sensing module includes at least one chemical detecting sensor for detecting chemical emissions or reactions. In an embodiment, the at least one chemical detecting sensor is used to identify the presence of the human or animal. In an embodiment, the at least one chemical detecting sensor includes at least one of the group containing: carbon dioxide sensor; humidity sensor; and volatile organic compounds (VOC) sensor.

In an embodiment, the sensing module includes at least one electric field sensor for detecting local electric field disturbances. In an embodiment, wherein the at least one electric field sensor is used to identify electrical properties of the human or animal. In a further embodiment, the at least one electric field sensor includes at least one electrode to detect capacitance changes. In another embodiment, the at least one electric field sensor includes an array of electrodes.

In an embodiment, the sensing module includes at least one physical disturbance sensor for detecting local physical disturbances. In an embodiment, the at least one physical disturbance sensor is used to identify local weight changes through contact with the human or animal. In a further embodiment, the at least one physical disturbance sensor is a pressure sensor.

In an embodiment, the sensing module includes at least one active or passive signal detecting sensor for detecting other active or passive signals. In an embodiment, the at least one active or passive signal detecting sensor is used to identify a label attached to the human or animal. In a further embodiment, the label includes a transponder or beacon. In embodiments, the label includes a radio-frequency identification tag, an infrared beacon, an ultrasonic beacon, or a radiofrequency beacon.

In an embodiment, the disinfectant operation is an interruptible process.

In an embodiment, the system includes a housing for containing the disinfectant module, the sensing module and a processing module. In an embodiment, the housing is configured to be mountable to a wall. In an alternate embodiment, the housing is configured to be mountable to a ceiling.

In another embodiment, the system includes a first housing for containing the disinfectant module, a second housing for containing the sensing module, and a third housing for containing a processing module.

In an embodiment, the disinfectant module includes at least one Ultra Violet light source. In an embodiment, the Ultra Violet light source is at least one of the group including: an Ultra Violet A (UV-A) light source; an Ultra Violet B (UV-B) light source; and an Ultra Violet C (UV-C) light source.

In an embodiment, the disinfectant module includes at least one micro-biocidal chemical source.

In an embodiment, the system includes a dosage control module for monitoring dosage information derived from disinfectant operations during a predefined operation period. In an embodiment, the dosage control module recalibrates the disinfectant module to change the disinfectant operation based on the monitored dosage information. In a further embodiment, the disinfectant operation includes a timing component and an intensity component, and the recalibration includes adjusting one or more of the timing component and the intensity component.

In an embodiment, the system including a processing module for receiving and integrating data from the sensing module, and communicating with the disinfectant module and dosage control module.

In accordance with a second aspect of the present invention there is provided a disinfectant method including:
  providing a disinfectant module for carrying out a disinfectant operation when a predefined condition is met;
  providing a sensing module for sensing the presence of all substantially stationary and/or intermittently mobile humans or animals within an enclosed space, the sensing module including at least one sensor; and
  performing a disinfectant operation within the enclosed space when the predefined condition is met, wherein the predefined condition is the absence of a human or animal within the enclosed space.

In an embodiment, the sensing module includes a plurality of sensors. In a further embodiment, at least one of the plurality of sensors is operatively associated with one another. In another embodiment, each of the plurality of sensors are operatively associated with one another.

In an embodiment, the sensing module includes at least one energy emission detecting sensor. In an embodiment, the step of providing a sensing module is followed by an additional step of using the at least one energy emission detecting sensor to identify shape and form of the human or animal.

In an embodiment, the at least one energy emission detecting sensor includes an imaging sensor. In an embodiment, the imaging sensor is a long wavelength infrared sensor.

In an embodiment, the step of providing a sensing module is followed by an additional step of using the at least one energy emission detecting sensor to identify macro-movement of the human or animal. In an embodiment, the at least one energy emission detecting sensor includes a passive infrared (PIR) sensor.

In an embodiment, the step of providing a sensing module is followed by an additional step of using the at least one energy emission detecting sensor to identify sound from the presence of the human or animal. In an embodiment, the at least one energy emission detecting sensor includes at least one microphone. In further embodiments, the at least one energy emission detecting sensor includes array of microphones.

In an embodiment, the step of providing a sensing module is followed by an additional step of using the at least one energy emission detecting sensor to identify vibration from the presence of the human or animal. In an embodiment, the at least one energy emission detecting sensor includes at least one an accelerometer.

In an embodiment, the step of providing a sensing module is followed by an additional step of using the at least one energy emission detecting sensor to identify a temperature change caused by the presence of the human or animal. In an embodiment, the at least one energy emission detecting sensor includes at least one temperature sensor. In a further embodiment, the at least one temperature sensor is a thermometer.

In an embodiment, the sensing module includes at least one energy reflection, shadowing, transmission or absorption detecting sensor that detects energy reflection, shadowing, transmission or absorption.

In an embodiment, the step of providing a sensing module is followed by an additional step of using the at least one energy reflection, shadowing, transmission or absorption detecting sensor to identify shape and form of the human or animal. In an embodiment, the at least one energy reflection, shadowing, transmission or absorption detecting sensor includes at least one imaging sensor. In a further embodiment, the at least one imaging sensor is a visible light or short wavelength infrared camera. In another embodiment, the at least one energy reflection, shadowing, transmission or absorption detecting sensor includes at least one radar sensor.

In an embodiment, the step of providing a sensing module is followed by an additional step of using the at least one energy reflection, shadowing, transmission or absorption detecting sensor to identify macro-movement of the human or animal. In an embodiment, the at least one energy reflection, shadowing, transmission or absorption detecting sensor includes a ranging sensor. In a further embodiment, the ranging sensor is one of the group containing: a ranging radar sensor, an ultrasonic sensor or a laser sensor.

In an embodiment, the step of providing a sensing module is followed by an additional step of using the at least one energy reflection, shadowing, transmission or absorption detecting sensor to identify micro-movement of the human or animal. In an embodiment, the at least one energy reflection, shadowing, transmission or absorption detecting sensor includes a Doppler sensor such as a Doppler radar, ultrasonic or laser sensor.

In an embodiment, the sensing module includes at least one chemical detecting sensor for detecting chemical emissions or reactions. In an embodiment, the step of providing a sensing module is followed by an additional step of using the at least one chemical detecting sensor to identify the presence of the human or animal. In an embodiment, the at least one chemical detecting sensor includes at least one of the group containing: carbon dioxide sensor; humidity sensor; and volatile organic compounds (VOC) sensor.

In an embodiment, the sensing module includes at least one electric field sensor for detecting local electric field disturbances. In an embodiment, the step of providing a sensing module is followed by an additional step of using the at least one electric field sensor to identify electrical properties of the human or animal. In a further embodiment, the at least one electric field sensor includes at least one electrode to detect capacitance changes. In another embodiment, the at least one electric field sensor includes an array of electrodes.

In an embodiment, the sensing module includes at least one physical disturbance sensor for detecting local physical disturbances. In an embodiment, the step of providing a sensing module is followed by an additional step of using the at least one physical disturbance sensor to identify local weight changes through contact with the human or animal. In a further embodiment, the at least one physical disturbance sensor is a pressure sensor.

In an embodiment, the sensing module includes at least one active or passive signal detecting sensor for detecting other active or passive signals. In an embodiment, the step of providing a sensing module is followed by an additional step of using the at least one active or passive signal detecting sensor to identify a label attached to the human or animal. In a further embodiment, the label includes a transponder or beacon. In embodiments, the label includes a radio-frequency identification tag, an infrared beacon, an ultrasonic beacon, or a radiofrequency beacon.

In an embodiment, the disinfectant operation is an interruptible process.

In an embodiment, the method includes the additional step of providing a housing for containing the disinfectant module, the sensing module and a processing module. In an embodiment, the housing is configured to be mountable to a wall. In an alternate embodiment, the housing is configured to be mountable to a ceiling.

In another embodiment, method includes the additional step of providing a first housing for containing the disinfectant module, a second housing for containing the sensing module, and a third housing for containing a processing module.

In an embodiment, the disinfectant module includes at least one Ultra Violet light source. In an embodiment, the Ultra Violet light source is at least one of the group including: an Ultra Violet A (UV-A) light source; an Ultra Violet B (UV-B) light source; and an Ultra Violet C (UV-C) light source.

In an embodiment, the disinfectant module includes at least one micro-biocidal chemical source.

In an embodiment, the method includes the additional step of providing a dosage control module for monitoring dosage information derived from disinfectant operations during a predefined operation period. In an embodiment, the method includes the additional step of recalibrating, by the dosage control module, the disinfectant module to change the disinfectant operation based on the monitored dosage information. In a further embodiment, the disinfectant operation includes a timing component and an intensity component, and the recalibration step further includes adjusting one or more of the timing component and the intensity component.

In an embodiment, the method includes the additional step of providing a processing module for receiving and integrating data from the sensing module, and communicating with the disinfectant module and dosage control module.

In accordance with a third aspect of the present invention there is provided a sensing system for sensing the presence of at least one substantially stationary and/or intermittently mobile human or animal within an enclosed space, the system being operatively associated with a disinfectant process, the system including:
- at least one sensor;
  - wherein the disinfectant process will be disabled when the system senses the presence of at least one substantially stationary and/or intermittently mobile human or animal.

In an embodiment, the system includes a plurality of sensors. In a further embodiment, at least one of the plurality of sensors is operatively associated with at least another one of the plurality of sensors. In another embodiment, each of the plurality of sensors are operatively associated with one another.

In an embodiment, the plurality of sensors includes at least one energy emission detecting sensor. In an embodiment, the at least one energy emission detecting sensor is used to identify shape and form of the human or animal.

In an embodiment, the at least one energy emission detecting sensor includes an imaging sensor. In an embodiment, the imaging sensor is a long wavelength infrared sensor.

In an embodiment, the at least one energy emission detecting sensor is used to identify macro-movement of the human or animal. In an embodiment, the at least one energy emission detecting sensor includes a passive infrared (PIR) sensor.

In an embodiment, the at least one energy emission detecting sensor is used to identify sound from the presence of the human or animal. In an embodiment, the at least one energy emission detecting sensor includes at least one microphone. In further embodiments, the at least one energy emission detecting sensor includes array of microphones.

In an embodiment, the at least one energy emission detecting sensor is used to identify vibration from the presence of the human or animal. In an embodiment, the at least one energy emission detecting sensor includes at least one an accelerometer.

In an embodiment, the at least one energy emission detecting sensor is used to identify a temperature change caused by the presence of the human or animal. In an embodiment, the at least one energy emission detecting sensor includes at least one temperature sensor. In a further embodiment, the at least one temperature sensor is a thermometer.

In an embodiment, the plurality of sensors includes at least one energy reflection, shadowing, transmission or absorption detecting sensor that detects energy reflection, shadowing, transmission or absorption.

In an embodiment, the at least one energy reflection, shadowing, transmission or absorption detecting sensor is used to identify shape and form of the human or animal. In an embodiment, the at least one energy reflection, shadowing, transmission or absorption detecting sensor includes at least one imaging sensor. In a further embodiment, the at least one imaging sensor is a visible light or short wavelength infrared camera. In another embodiment, the at least one energy reflection, shadowing, transmission or absorption detecting sensor includes at least one radar sensor.

In an embodiment, the at least one energy reflection, shadowing, transmission or absorption detecting sensor is used to identify macro-movement of the human or animal.

In an embodiment, the at least one energy reflection, shadowing, transmission or absorption detecting sensor includes a ranging sensor. In a further embodiment, the ranging sensor is one of the group containing: a ranging radar sensor, an ultrasonic sensor or a laser sensor.

In an embodiment, the at least one energy reflection, shadowing, transmission or absorption detecting sensor is used to identify micro-movement of the human or animal. In an embodiment, the at least one energy reflection, shadowing, transmission or absorption detecting sensor includes a Doppler sensor such as a Doppler radar, ultrasonic or laser sensor.

In an embodiment, the plurality of sensors includes at least one chemical detecting sensor for detecting chemical emissions or reactions. In an embodiment, the at least one chemical detecting sensor is used to identify the presence of the human or animal. In an embodiment, the at least one chemical detecting sensor includes at least one of the group containing: carbon dioxide sensor; humidity sensor; and volatile organic compounds (VOC) sensor.

In an embodiment, the plurality of sensors includes at least one electric field sensor for detecting local electric field disturbances. In an embodiment, wherein the at least one electric field sensor is used to identify electrical properties of the human or animal. In a further embodiment, the at least one electric field sensor includes at least one electrode to detect capacitance changes. In another embodiment, the at least one electric field sensor includes an array of electrodes.

In an embodiment, the plurality of sensors includes at least one physical disturbance sensor for detecting local physical disturbances. In an embodiment, the at least one physical disturbance sensor is used to identify local weight changes through contact with the human or animal. In a further embodiment, the at least one physical disturbance sensor is a pressure sensor.

In an embodiment, the plurality of sensors includes at least one active or passive signal detecting sensor for detecting other active or passive signals. In an embodiment, the at least one active or passive signal detecting sensor is used to identify a label attached to the human or animal. In a further embodiment, the label includes a transponder or beacon. In embodiments, the label includes a radio-frequency identification tag, an infrared beacon, an ultrasonic beacon, or a radiofrequency beacon.

In an embodiment, the disinfectant process is an interruptible process.

In an embodiment, the system includes a housing for containing the plurality of sensors, a disinfectant module, and a processing module. In an embodiment, the housing is configured to be mountable to a wall. In an alternate embodiment, the housing is configured to be mountable to a ceiling.

In another embodiment, the system includes a first housing for containing the disinfectant module, a second housing for containing the sensing module, and a third housing for containing a processing module.

In an embodiment, the disinfectant module includes at least one Ultra Violet light source. In an embodiment, the Ultra Violet light source is at least one of the group including: an Ultra Violet A (UV-A) light source; an Ultra Violet B (UV-B) light source; and an Ultra Violet C (UV-C) light source.

In an embodiment, the disinfectant module includes at least one micro-biocidal chemical source.

In an embodiment, the system includes a dosage control module for monitoring dosage information derived from disinfectant operations during a predefined operation period.

In an embodiment, the dosage control module recalibrates the disinfectant module to change the disinfectant operation based on the monitored dosage information. In a further embodiment, the disinfectant operation includes a timing component and an intensity component, and the recalibration includes adjusting one or more of the timing component and the intensity component.

In an embodiment, the system including a processing module for receiving and integrating data from the plurality of sensors, and communicating with the disinfectant module and dosage control module.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Preferred embodiments of the disclosure will now be described, by way of example only, with reference to the accompanying drawings in which.

DETAILED DESCRIPTION

Figure 1A:
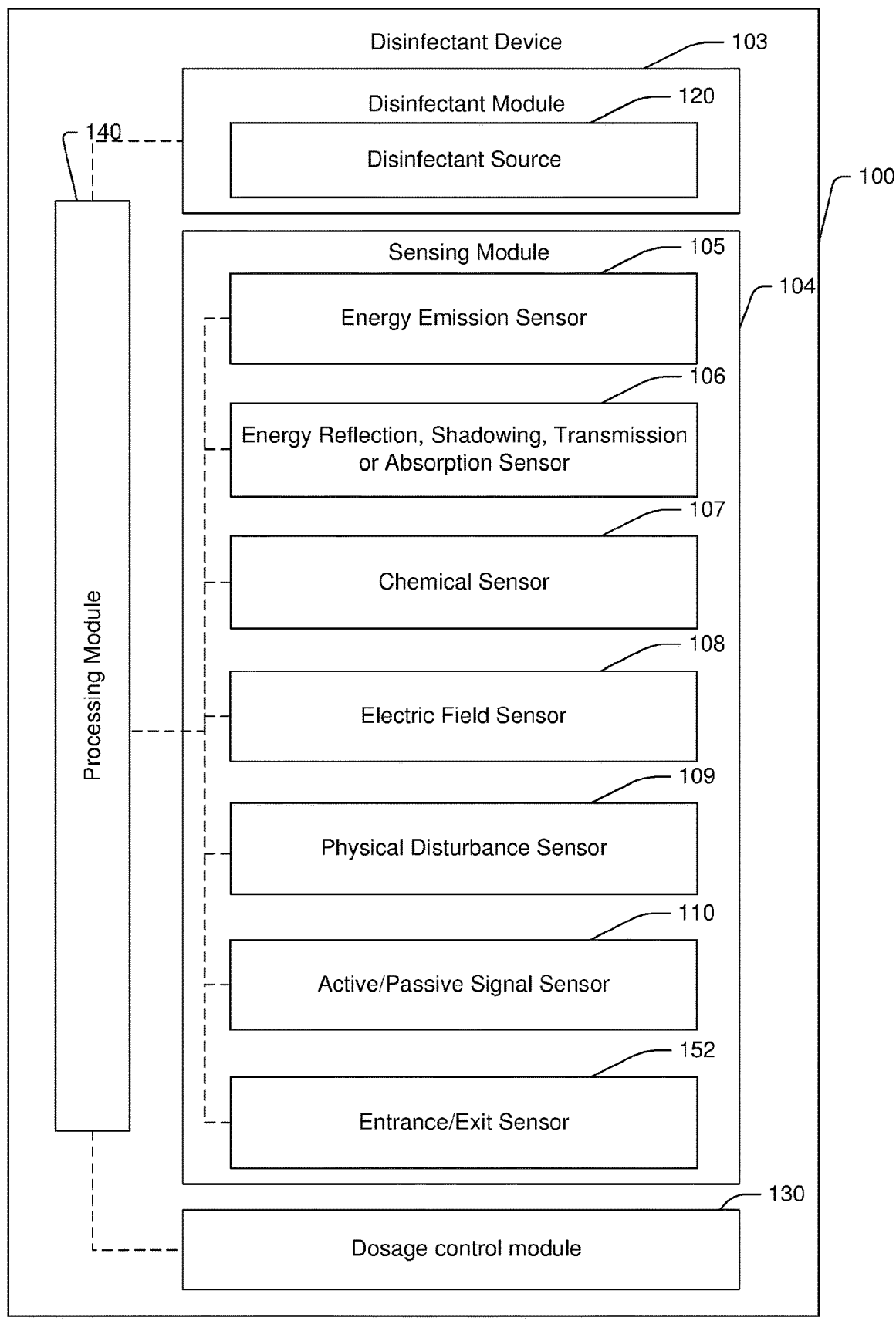
FIG. 1A is a conceptual block diagram of a disinfectant device in accordance with an embodiment of the invention.
Figure 1B:
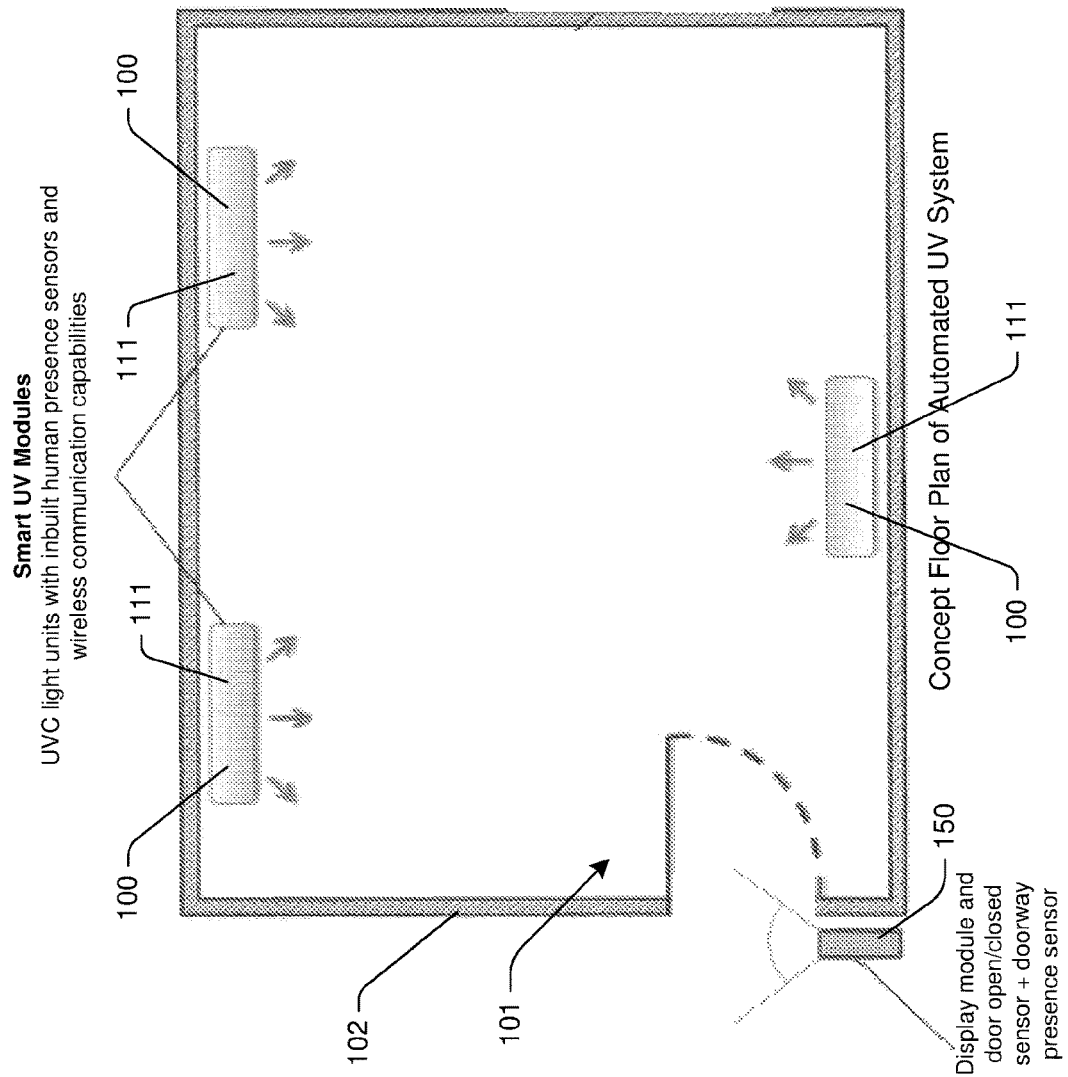
FIG. 1B is a schematic diagram of three disinfectant devices of FIG. 1A, shown mounted within a room.

Referring initially to FIGS. 1A and 1B, there is provided a disinfectant system in the form of an autonomous device 100 for performing a disinfectant operation within an enclosed space 101 defined by the walls, ceiling and floor of a room 102 when a predefined condition, in the form of the absence of a human being (not shown) within room 102, is met. The purpose of the system is environmental decontamination and specifically to inactivate pathogenic organisms.

Device 100 includes a disinfectant module 103 for carrying out the disinfectant operation when there is an absence of a human being within room 102. A sensing module 104 is provided for sensing the presence of a substantially stationary human being within room 102. Sensing module 104 includes:

An energy emission detecting sensor 105 to detect energy emitted by humans;

An energy reflection, shadowing, transmission or absorption detecting sensor 106 to detect energy reflected, shadowed, transmitted or absorbed by humans;

A chemical detecting sensor 107 to detect chemicals emitted by humans;

An electric field sensor 108 to detect local electric field disturbances, such as those created by the presence of a human;

A physical disturbance sensor 109 to detect local physical disturbances, such as a pressure sensor to detect the presence of a human; and An active or passive signal detecting sensor 110 to detect other active or passive signals from instrumented subjects.

Disinfectant module 103 includes a disinfectant source 120, which is preferably an ultra violet (UV) light source in the form of an ultra violet C (UV-C) source. One of the advantageous aspects of disinfecting using UV light is that once the light turns off, it is safe for a person to enter the space into which UV light was previously directed. Equally as advantageous is that as soon as UV-C source 120 is activated, it provides immediate germicidal activity. As such, the disinfectant operation is an interruptible process in the sense that the process can be paused to allow the space to be used, and recommenced once the person has left the space. Furthermore, the output of UV-C source 120 can be tailored.

UV light sources can include any modules which emit UV radiation. In embodiments, these include, but not limited to, mercury vapour tubes (low and medium pressure) and UV LEDs. As noted above in this embodiment, the UV-C spectrum will be utilised from 200-280 nm for peak germicidal activity.

In other embodiments, other sources of electromagnetic radiation at a wavelength and intensity that is microbiocidal are utilized including, for example, UV-A, UV-B or 405 nm light. In yet other embodiments, a combination of the aforementioned sources of electromagnetic radiation at a wavelength and intensity that is microbiocidal are utilized.

In alternate embodiments, other types of disinfectant operations are used, for example, microbiocidal chemicals released into the air in room 102.

The disinfectant operation will be delivered to room 102 in a piecemeal manner as device 100 can utilize short opportunities that may arise from occupants briefly leaving room 102. In alternate embodiments, the disinfectant operation will be delivered to room 102 in other than a piecemeal manner. In addition, the system can deliver a full dose when a space is purposely evacuated, such as for terminal decontamination after a patient is discharged from a room.

Device 100 includes a dosage control module 130 which maintains a running record of the amount of UV energy that has been delivered to space 101 during the immediate history, for example the past 24 hours. This information is used to determine how long the UV lamps will be activated when a safe opportunity arises. The system will maintain a specific target dose level for room 102. Target dose refers to how many Joules of UV radiation is delivered to the room over some nominal period (for example, 24 hours). This target dose will vary from space to space and will be determined from factors including: room size and geometry; UV lamp power; materials present; and time of occupancy of the space, amongst others. In some embodiments, there is an option to input data to the system which could affect target dosage, for example, whether a patient is carrying a high risk transmittable bacterial infection (such as *Clostridium difficile*, for example).

The disinfectant operation includes a timing component and an intensity component, the latter of which is based on the intensity of source 120. Recalibration of disinfectant module 103 includes adjusting the timing component and/or the intensity component based on the set amount of time and within that time, how long the disinfectant operation was running and at what intensity.

It will be appreciated that the minimum level of disinfecting will substantially prevent the spread of infections to human beings. However, in other embodiments, greater levels of disinfection will be utilised. The highest such level is complete sterilisation of room 102. However, in most scenarios, total sterilisation is not required and will not be sought due to power conservation reasons.

As noted above sensor 105 detects energy emissions in order to identify the shape and form of a human being. Sensor 105 includes a non-contact thermal imaging sensor. In other embodiments, sensor 105 includes a non-contact thermal temperature sensor. In another embodiment, sensor 105 includes an infrared sensor in the form of a long wavelength infrared camera. In yet other embodiments, sensor 105 is a combination of one or more of: a non-contact thermal imaging sensor; a non-contact thermal temperature sensor; and an infrared sensor.

Long wavelength infrared cameras utilise thermal computer vision image processing for detecting infrared thermal heat signatures of human beings within room 102. Long wavelength infrared (8-14 μm wavelength) cameras include Forward Looking Infrared (FLIR) Lepton cores. Such cameras are suitable for providing a thermographic video feed. This video feed is used as the subject of image processing functions tailored for detecting the thermal signature of a human body. Additionally, in some embodiments, infrared sensors also include a non-contact temperature sensor, such as a non-imaging thermal sensor. In one embodiment, the long wavelength infrared camera provides the primary sensing and the non-contact temperature sensor provides additional sensing to supplement the primary sensing, adding an additional layer of safety and efficacy to the system. In other embodiments, the non-contact temperature sensor provides the primary sensing.

Sensor 105 is also able to detect energy emissions in order to identify macro-movement of a human being. In such embodiments, sensor 105 includes a non-image passive infrared (PIR) sensor for providing motion sensing. In other embodiments, other than PIR sensors are used.

In other embodiments, tracking of macro-movements is carried out using a combination of imaging processing and long wavelength infrared cameras.

Sensor 105 is further able to detect energy emissions in order to identify sound produced by a human being. In such embodiments, sensor 105 includes an array of microphones.

Furthermore, sensor 105 is able to detect energy emissions in order to identify vibrations produced by a human being. In such embodiments, sensor 105 includes an accelerometer.

Sensor 106 detects energy reflection, shadowing, transmission or absorption in order to identify the shape and form of a human being. Sensor 106 includes an imaging sensor in the form of a visible light camera. In an alternate embodiment, the imaging sensor is a short wavelength infrared camera. In yet other embodiments, sensor 106 is a radar sensor.

Furthermore, sensor 106 is able to detect energy reflection, shadowing, transmission or absorption in order to identify macro-movement of a human being. In such embodiments, sensor 106 includes a ranging sensor, in the form of a radar sensor. In an alternate embodiment, the ranging sensor is an ultrasonic sensor. In yet another embodiment, the ranging sensor is a laser sensor. In yet another embodiment, the ranging sensor includes one or more of: a radar sensor, an ultrasonic sensor and a laser sensor.

Sensor 106 is able to detect energy reflection, shadowing, transmission or absorption in order to identify micro-movement of a human being. In such embodiments, sensor 106 includes a non-contact sensor in the form of a Doppler sensor, more specifically in the form of a Doppler radar sensor. In another embodiment, the Doppler sensor is a Doppler ultrasonic sensor. In yet another embodiment, the Doppler sensor includes a Doppler laser sensor for laser scanning. In yet another embodiment, the Doppler sensor includes one or more of: a Doppler radar sensor, a Doppler ultrasonic sensor and a Doppler laser sensor.

As alluded to above, sensor 107 aims to detect the metabolic activity of a human being, particularly in the form of chemical elements that are emitted by the human body and chemical reactions signifying the presence of a live human being. Sensor 107 includes a carbon dioxide detecting sensor. In another embodiment, sensor 107 includes a humidity sensor for sensing water vapour. In yet another embodiment, sensor 107 includes a volatile organic compounds (VOC) sensor. In an alternate embodiment, sensor 107 includes a combination of: carbon dioxide detection, humidity sensing and VOC sensing.

Sensor 108 is able to detect local electric field disturbances in the presence of a human being. Sensor 108 includes a capacitance sensor which itself includes electrodes to for detecting the local changes in capacitance.

As noted previously, sensor 109 aims to detect local physical disturbances caused by contact from a human being and necessitates physical contact with a human being in order to sense that human being. Sensor 109 takes the form of one or more pressure contact sensors used, for example, on hospital beds. Such contact sensors necessitate manual fitting of an additional device physically separated from device 100.

As noted above, other active or passive signal detecting sensors 110 are also utilised where required. These include devices or labels attachable to human beings including transponders or beacons such as radio-frequency identification (RFID) tags, infrared beacons, ultrasonic beacons and radiofrequency beacons, amongst others.

It will be appreciated that different embodiments will utilise different combinations of sensors 105 to 110 depending on the requirements or certain situations and environments. Furthermore, in different embodiments, each of sensors 105 to 110 includes one or more of the specific sensor devices discussed above. Furthermore still, in different embodiments, each of sensors 105 to 110 includes a plurality of one or more of the specific sensor devices discussed above. That is:

Energy emission detecting sensor 105 in different embodiments includes a combination of shape and form sensors (which in different embodiments includes a combination of different imaging sensors), macro-movement sensors, sounds sensors, vibration sensors and temperature change sensors.

Energy reflection, shadowing, transmission or absorption detecting sensor 106 in different embodiments includes a combination of shape and form sensors (which in different embodiments includes a combination of visible light imaging sensors, short wavelength IR cameras and ultra-wide band radar sensors), macro-movement sensors (which in different embodiments includes a combination of ranging sensors such as radar, ultrasonic and laser) and micro-movement sensors (which in different embodiments includes a combination of Doppler sensors such as radar, ultrasonic and laser).

Chemical detecting sensor 107 in different embodiments includes a combination of metabolic activity sensors such as carbon dioxide sensors, humidity sensors and VOC sensors.

Electric field sensor 108 in different embodiments includes a combination of different electrical property sensors such as capacitance change sensors.

Physical disturbance sensor 109 in different embodiments includes a combination of different pressure contact sensors.

Active or passive signal detecting sensor 110 in different embodiments includes a combination of different devices or labels attachable to human beings, including transponders or beacons such as RFID tags, infrared beacons, ultrasonic beacons and radiofrequency beacons, amongst others.

Most non-contact human detection sensors rely on some small amount of motion in order to detect human presence. Using a combination of sensors as discussed above (such as infrared sensors and micro-movement sensors) applied to room 102, the system is able to detect the presence of a person even if they are completely still and covered, for example, under bedding.

It is again emphasised that a many number of sensors can be utilised to provide varying levels of certainty of a correct reading. Given the adverse health effects of exposing UV or indeed some disinfectant chemicals to a person, there must be a high threshold that must be met to all but ensure that there are no person or persons present when the disinfection operation is occurring. As such, the level of certainty of a correct reading will generally increase with the increased usage of different numbers and types of sensors in varying positions around a room.

The sensors will be positioned to monitor the entire enclosed space 101. In some embodiments, the sensors are positioned to be monitoring in the direction of the emitted UV radiation or disinfectant chemicals. This ensures the direct path of emitted disinfectant is being constantly sensed for any human presence. In other embodiments, the sensors will be positioned to be monitoring in a direction other than that of the emitted disinfectant. In yet other embodiments, some sensors will be positioned to be monitoring in the direction of the emitted disinfectant and other sensors will monitor in other directions. The size and layout of room 102, as well as the objects within it, will factor into the position of the sensors.

Device 100 further includes a processing module 140, in the form of a microprocessor that is in electrical communication with disinfectant module 103, sensor module 104 and dosage control module 130. Processing module 140 utilises algorithms to receive sensor data from sensor module 104 and mathematically calculate the probability that a human being is present in room 102. Processing module 140 also utilises algorithms to determine the confidence that a discernible thermal mass detected by sensor module 104 is indeed a human being. Low confidence readings may have a high probability of being inaccurate. To avoid inaccurate readings governing the system, all sensor data shall pass through a probability filter which will discard low confidence readings. For example, there may be heated objects or medical devices within room 102 which emit significant amounts of infrared radiation. Mask subtraction techniques can be implemented to minimise false positive triggers. This involves subtracting a thermographic image of room 102 when unoccupied from future image frames of interest, filtering out any warm stationary, non-human objects which may be emitting IR radiation. Also there may be mechanical movement (such as fans) in the room that may affect a micro movement sensor. In some embodiments, algorithms that look for the distinctive pattern of human breathing are implemented to overcome this.

In some embodiments, image processing is used to isolate any thermal body which may be a human body. In some of those embodiments, feature detection and recognition algorithms will be incorporated into this image processing. Ratios of feature sizes (width:height) and the total number of pixels a mass occupies all provide valuable data.

If the probability is such that a person is not in the room, processing module 140 will communicate with disinfectant module 103 that it can commence the disinfectant operation, whilst also communicating with dosage control module 130. Dosage control module 130 essentially monitors how long source 120 is activated and how much power is used by source 120. The situation may be such that device 100 should shut off even if the room is absent of human beings at a point when room 102 is deemed to be completely sterilized or at an appropriate level of disinfection, as will be determined by dosage control module 130. Furthermore, dosage module 130 can also provide an indication that deems room 102 to require a terminal clean, whereby the system prompts a staff member to arrange for the terminal clean.

In embodiments, dosage module 130 includes UV power sensors for sensing exactly how much UV light has been exposed in the room. This sensing will provide further information from which dosage module 130 can make a judgement on the UV required in room 102. In other embodiments utilizing chemical disinfectants, dosage module 130 includes chemical sensors to sense how much disinfectant has been circulated and makes a judgement in a similar fashion to embodiments using UV.

The system will necessarily have a high safety threshold as information from several sensing technologies will be fused together to accurately protect against false negative triggers, that is, the system falsely believing the space is empty.

It is noted that, in embodiments, an additional layer of manual protection is included. For example, once the system is ready to start the disinfectant operation, that is where no human presence is sensed in room 102, system 100 will require an authorisation check before actually starting disinfectant operation. This authorisation check takes the form of an RFID tag that can be swiped at an authorisation point to confirm it is safe to proceed with the disinfectant operation. In other embodiments, the authorisation check takes the form of passcode to be entered into another authorisation point such as a keypad. However, it is emphasised that if the presence of a live human being is detected, providing the authorisation check will not result in the disinfectant operation. This will only occur if no human presence is sensed in room 102.

Some of the sensors, particularly the infrared sensors are able to detect if its field of view has been obscured or blocked. An absence of this feature could lead to the system suggesting un-occupancy of a space when in fact the cameras field of view has simply been blocked by some article.

Device 100 includes a housing 111 that, in some embodiments, contains disinfectant module 103 and sensing module 104. It will be appreciated that, in various embodiments, the substantive material of housing 111 is plastics, metal, a combination of plastics and metal, or others materials. In the embodiment illustrated in FIG. 1B, housing 111 is configured to be mountable to one or more walls or surfaces of room 102. In other embodiments, housing 111 is configured to be mountable or retrofitted to the ceiling of room 102. In other embodiments, housing 111 contains any combination of the disinfectant module 103, sensing module 104, processing module 140 and dosage control module 130. In yet other embodiments, each module has a separate housing, or some modules may be combined in the same housing while other modules are separately housed.

In other embodiments where processing module 140 is physically spaced apart from housing 111, processing module 140 is in wireless communication with disinfection module 103, sensor module 104 and dosage control module 130. However, in other embodiments, processing module 140 is hardwired to each of disinfection module 103, sensor module 104 and dosage control module 130. In various other embodiments, each of sensors 105 to 110 are housed in different spaced apart locations in different physical housings. In yet other various embodiments, some of those sensors are housed together, and others are not. For example, in one embodiment, sensor 105, sensor 106 and sensor 107 are in one housing, sensor 108 is in another housing, and sensors 109 and 110 are in a further separate housing. Furthermore, in some embodiments, the different types of sensors within sensors 105 to 110 are in a combination of different housings. There are a many number of permutations of sensors and components in general being housed separately or together with certain other components and it will be appreciated to a person skilled in the art that this will depend on many factors including the layout of room 102 itself.

Processor module 140 calculates required intensity and exposure time by assessing and factoring in how many people have been in the space and for how long.

Device 100 is designed to be confined to space 101 being monitored, and in different embodiments, is either permanently fixed in place, semi-portable or mobile. The placement of device 100 is generally determined during the installation phase. It is noted that in FIG. 1B, room 102 includes three wall-mounted devices 100. However, it will be appreciated that more or less than three devices but can be more or less as required.

Figure 2:
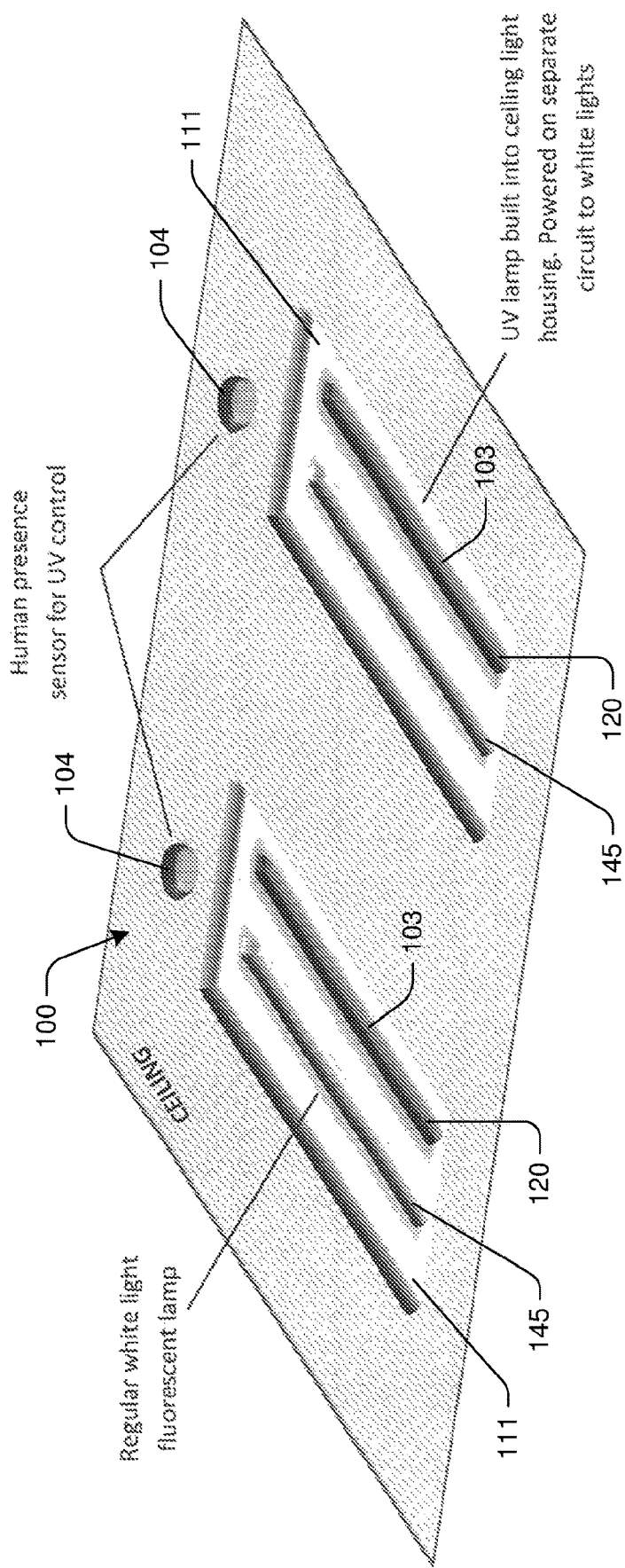
FIG. 2 is a perspective view of an embodiment of device of FIG. 1A.

Referring to FIG. 2, in this embodiment, device 100 also includes a regular white light fluorescent room lamp 145 but connected to a separate power circuit and separately controlled.

Figure 3:
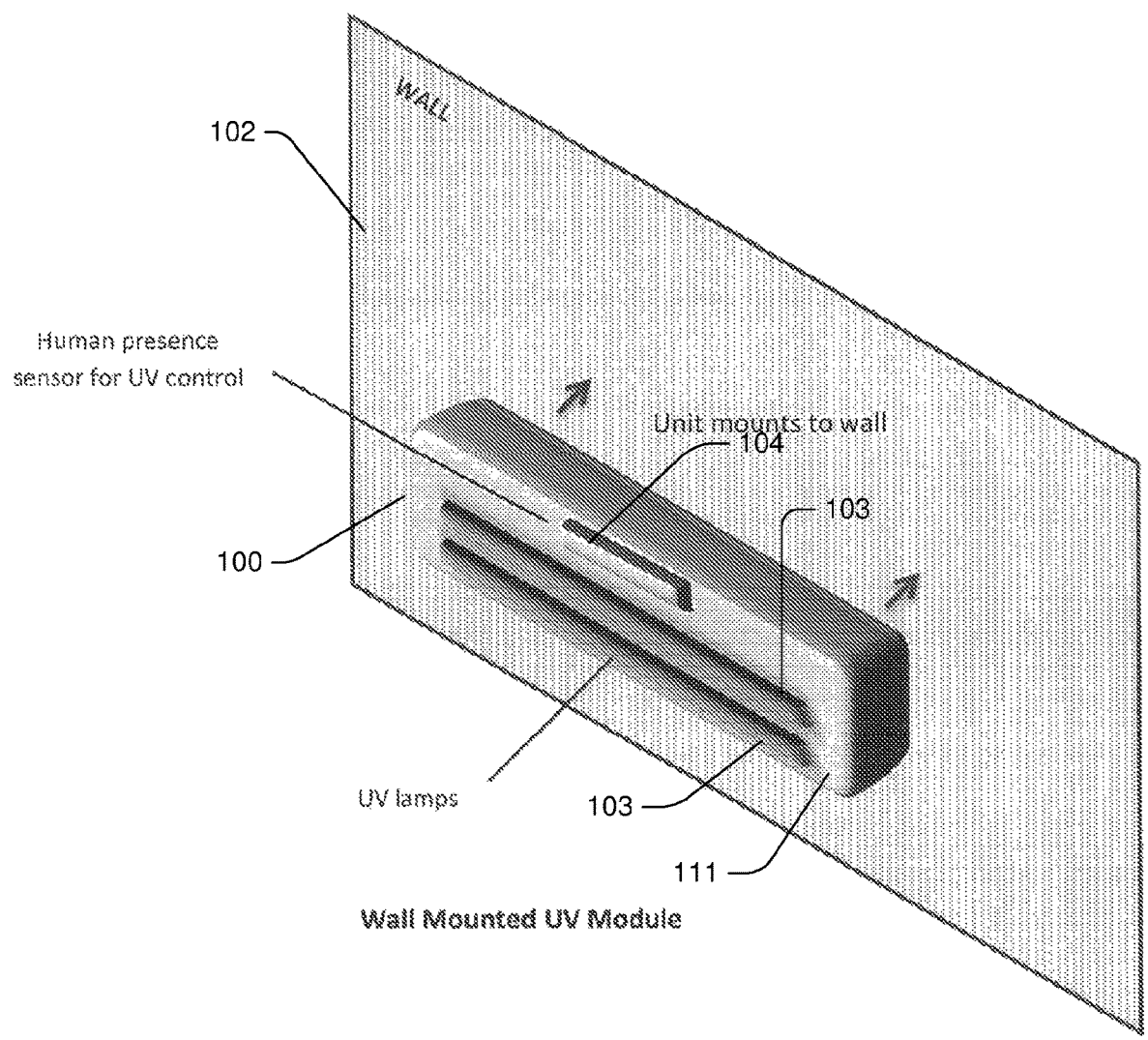
FIG. 3 is a perspective view of another embodiment of device of FIG. 1A.

Referring to FIG. 3, in this embodiment, device 100 is permanently physically mounted to a wall of room 102.

Figure 4:
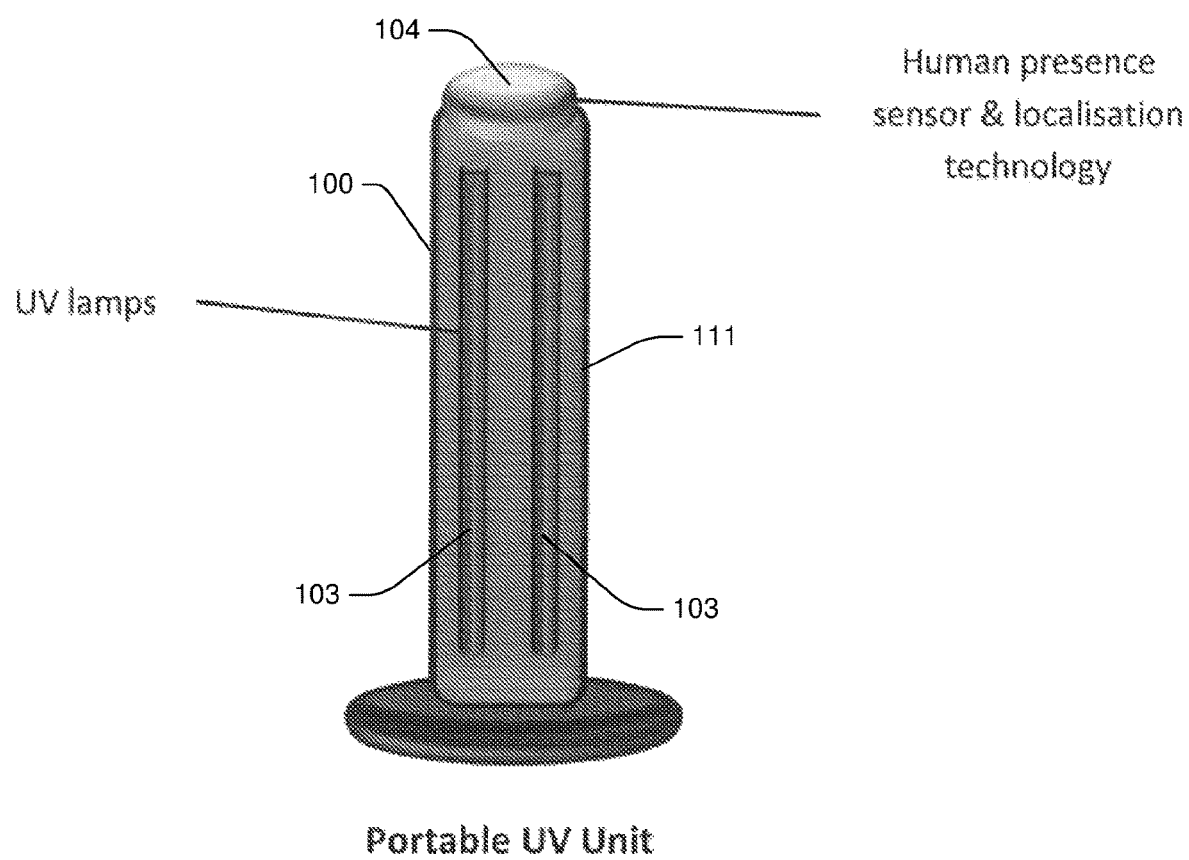
FIG. 4 is a perspective view of yet another embodiment of device of FIG. 1A.

Referring to FIG. 4, in this embodiment, device 100 is free standing and portable so the UV delivery can be somewhat adjusted in space 101. However, it is crucial that any portable units are not moved outside of the monitored space as this could lead to the UV sources being activated in the presence of people. In such embodiments, safety mechanisms are built into device 100 so that any unauthorized movement of a portable device 100 will disable the disinfectant operation until such time as an authorization process is completed to re-activate device 100. Similarly, such embodiments include a localisation technology to ensure the units remain positioned within the space being monitored by the system or to identify if the portable units have been moved outside space 101 that is being monitored. In some embodiments, this technology involves the use of beacons or fiducial markers on housing 111 of the portable device 100 which must be detected by an overseeing vision system or a type of electronic ranging system. This is to ensure that any portable unit moved outside of the monitored space are automatically deactivated so there is no chance of them being incorrectly activated in the presence of people.

Figure 5:
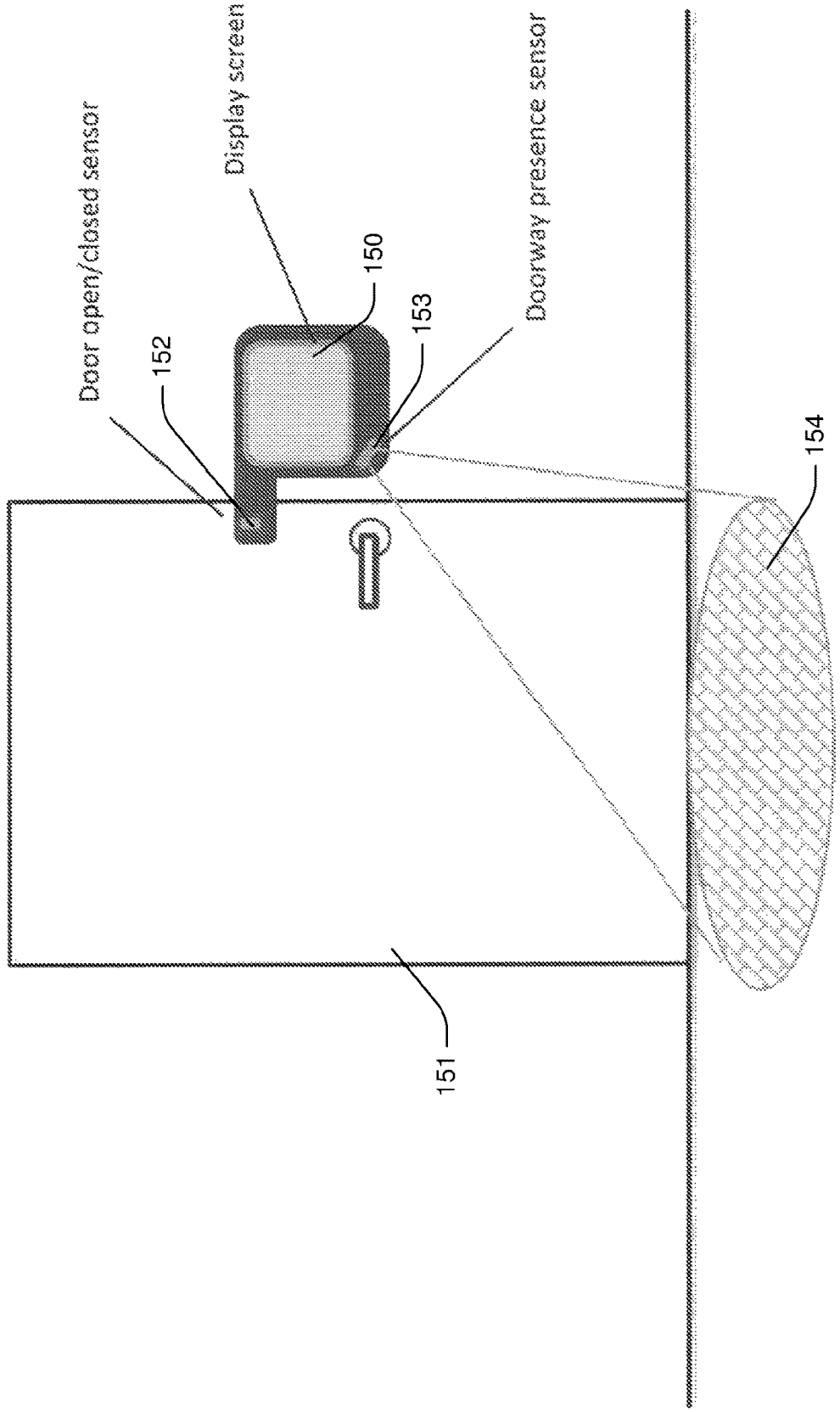
FIG. 5 is a perspective view outside an entrance door of a room to be monitored showing a display module and doorway presence sensor, with the door shown as closed.

Referring to FIGS. 1A and 1B and more specifically to FIG. 5, an information display unit 150 is included to display information regarding delivered UV and what level of decontamination can expected at any given time. In embodiments, suggestions can also be made as to when a room should be completely evacuated and allowed to run a full terminal disinfection cycle, these suggestions made in conjunction with dosage control module 130. Display unit 150 shall clearly indicate useful information on the graphics screen near a main entrance door 151 to room 102. In some embodiments, display unit 150 will incorporate a further entrance/exit sensor 152 to sense whether or not the entrance door is open or closed. This is critical in terms of safety, as the disinfectant operation cannot be turned on if the door is open as significant amounts of UV radiation could leak out into the corridor and potentially make contact with people.

Display unit 150 also houses a doorway presence sensor 153. This sensor will monitor a region 154 just outside of door 151 for shutting off the disinfectant operation before a person enters room 102.

In the illustrated embodiment, display unit 150 includes sensors 152 and 153, but it will be appreciated that in other embodiments, these sensors will be independent and spaced apart from display unit 150.

Each portable device 100 will have wireless communication capabilities.

Figure 6:
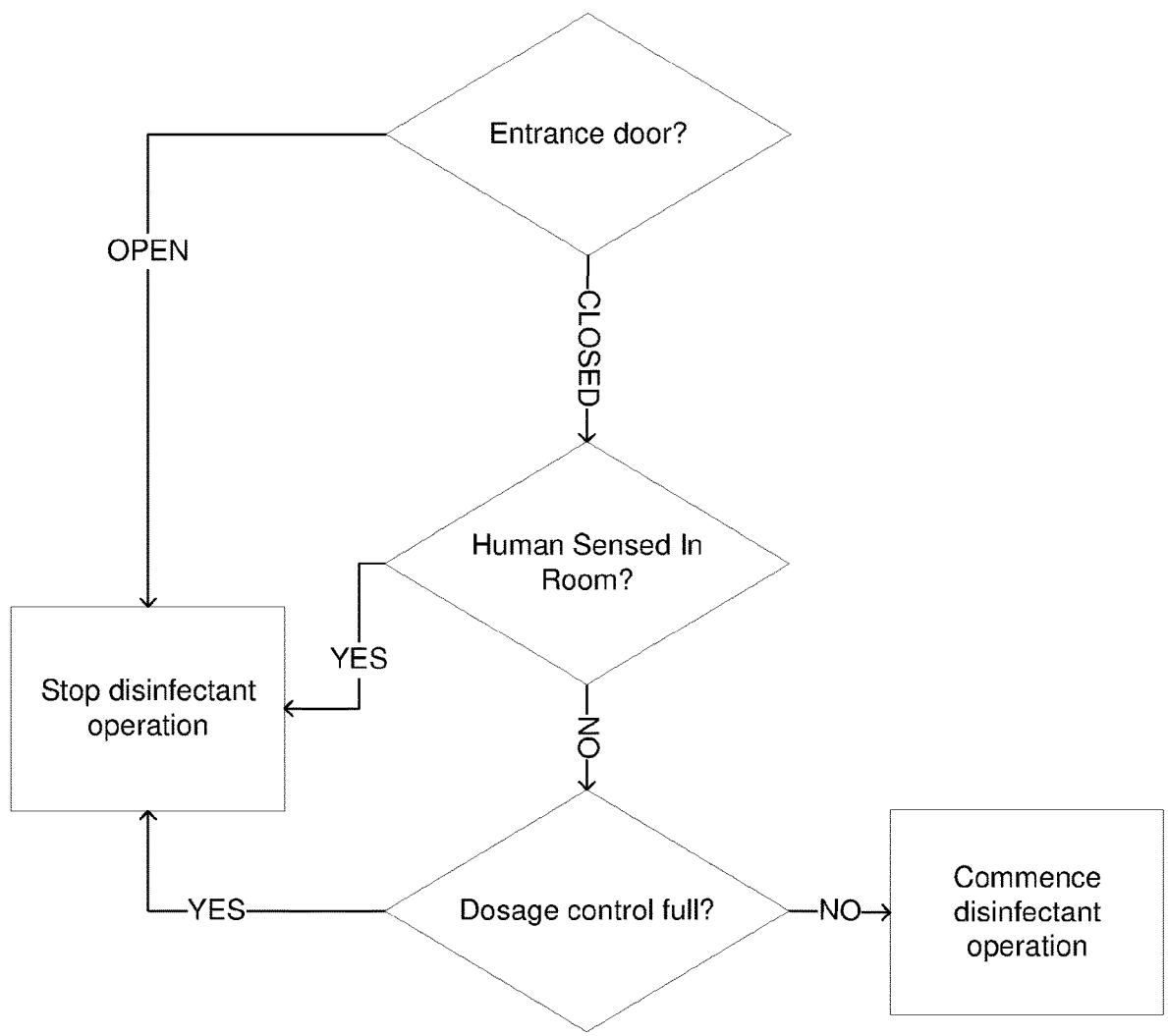
FIG. 6 is a flow chart demonstrating the working of an embodiment of the invention.

Referring to FIG. 6, a simplistic flow chart of the general operative steps of the disinfectant system is illustrated. The system will first check if entrance door 151 (is open or closed). If the door is open, the disinfectant operation ceases and continues to cease while the door is open. Once entrance door 151 is closed the system will check that no human beings or animals are sensed inside the room. As mentioned above, this process involves the output from the sensors being received and processed by the microprocessor to determine statistically if there is likely to be one or more human beings in room 102. If the microprocessor determines that there are no human beings in room 102, the system (by way if the microprocessor) will check dosage control module 130 to determine if room 102 has already received the maximum required dosage of disinfection and, if that is the case, the disinfectant operation ceases. Otherwise, the disinfectant operation will commence and continue to commence until a condition above is met to cease the operation.

It will be appreciated that in other embodiments, the system is safe to operate regardless of whether entrance door 151 is open or closed. In such embodiments, the system will strictly rely on checking that no humans or animals are sensed inside room 102.

Although the systems and methods described herein are mainly directed towards sensing the presence or absence of live human beings, it will be appreciated that the sensing could be used for other mammals and other warm-blooded creatures. For example, applications of the system could be used at a veterinarian practice for sensing the presence (or lack of a presence) of humans and animals.

Furthermore, the systems and methods described herein are mainly directed to use in hospitals or healthcare facilities. However, it is appreciated that other industries where contamination is of concern, such as the food processing and packaging industry, can utilize embodiments of the invention.

System 100, in particular processing module 140, incorporates computer components and software to control the functioning of the system. As such, appropriate safety protocols are included within the system to avoid a software error/bug from incorrectly turning a UV source on.

Furthermore, in embodiments, the system includes a data logging component for monitoring and recording in a database events and aspects of those events (such as timing and frequency of disinfectant operations). Such data is used for analysing a range of aspects of the system and the environment, such as work flows and power usage efficiencies, amongst others.

The systems described herein provide many advantages over the prior art, including:

- The disinfectant operation can be run whenever there is no person in the room, not just between occupancies of patients. For example, when a patient (and any other person in the room) goes and to rehabilitation, or goes to the bathroom, or leaves the room for any reason, the system can take advantage of the absence by performing the disinfectant operation during those times of absence. The room is constantly monitored to ensure than any moments of absence at any time can be utilised for this opportunistic disinfection.
- The constant monitoring and disinfecting at all available times makes for a more efficient use of time, as the manual operation requirement is significantly, and in some cases entirely, removed. This is due to the system not requiring to be set up prior to every single use, and substantially negating the need to move the equipment.
- The use of non-contact sensing alleviates the need to have the devices built into existing objects in the room. This make the system particularly suited to retrofitting into existing spaces.
- Workflows in a hospital environment are under significant time pressure, and any process that detrimentally impact on workflows will not be feasible. The system not only avoids disrupting workflows, it even improves workflows when compared to existing space disinfection systems. With existing devices, staff and/or operators are required to manually check the room, retrieve the disinfectant device, move the device into the room and manually activate the device. This labour-intensive manual work is significantly reduced and in some cases completely removed due to the present systems described.
- Specifically regarding the integrated setup using multiple specifically positioned devices (such as the setup of FIG. 1B), each device is placed so that substantially all of the surfaces in a room are disinfected. As such, the possibility of surfaces not receiving adequate disinfection is significantly reduced.
- The system is extremely safe in that it is designed to very accurately sense the presence of a person and shut off the disinfectant operation if a person is present or enters a room. Given the use of UV in the disinfectant operation, the system has no choice but to provide such a high safety threshold, given the health implications of being exposed to UV radiation. The use of multiple sensors to all but ensure the absence of a human being in the proposed area to disinfect allows this very high safety threshold to be met.
- The operator of prior known UV disinfectant devices no longer has to travel to storage areas, transport the large device to a space of interest, set up, run, ensure no one enters the space, pack up and finally transport back to storage. With the systems described herein, the operator may only need to close the door of a room and the system functions autonomously. In some embodiments, there may not even be a need for an operator due to the autonomous function of the system activating the disinfectant operation whenever there is no human presence sensed in the room.
- The system using such opportunistic disinfection of the present systems leads to an overall reduction in germ levels at all times. The system keeps the bioburden in check and generally at a level which has been shown to reduce HAIs.

Interpretation

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes an input device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a user machine in server-user network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while diagrams may only show a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that is for execution on one or more processors, e.g., one or more processors that are part of web server arrangement. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause the processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an exemplary embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media; a medium bearing a propagated signal detectable by at least one processor of one or more processors and representing a set of instructions that, when executed, implement a method; and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

We claim:

1. A hospital disinfectant system for automatically performing a disinfectant operation within an enclosed space when a predefined condition is met, the disinfectant system comprising:
   a disinfectant module comprising at least one micro-biocidal chemical source for carrying out the disinfectant operation when the predefined condition is met; and
   a sensing module including at least two sensors operable to sense a presence of a human or an animal within the enclosed space when the human or the animal is substantially still and covered under bedding, wherein the at least two sensors comprise a chemical sensor and a micro-movement sensor operable to detect micro-movements of a human or an animal when substantially still and covered under bedding;
   wherein the predefined condition is the absence of the human or the animal within the enclosed space.

2. The disinfectant system according to claim 1 wherein the sensing module further includes at least one energy emission detecting sensor wherein the at least one energy emission detecting sensor is used to identify one or more of the group comprising:
   shape and form of the human or the animal;
   macro-movement of the human or the animal;
   sound from the presence of the human or the animal;
   vibration from the presence of the human or the animal; and
   a temperature change caused by the presence of the human or the animal.

3. The disinfectant system according to claim 2 wherein the at least one energy emission detecting sensor includes an imaging sensor, wherein the imaging sensor is a long wavelength infrared sensor.

4. The disinfectant system according to claim 2 wherein the at least one energy emission detecting sensor includes a passive infrared (PIR) sensor.

5. The disinfectant system according to claim 2 wherein the at least one energy emission detecting sensor includes at least one microphone.

6. The disinfectant system according to claim 2 wherein the at least one energy emission detecting sensor includes at least one accelerometer.

7. The disinfectant system according to claim 2 wherein the at least one energy emission detecting sensor includes at least one temperature sensor, wherein the at least one temperature sensor is a thermometer.

8. The disinfectant system according to claim 1 wherein the sensing module further includes at least one energy reflection, shadowing, transmission or absorption detecting sensor that detects energy reflection, shadowing, transmission or absorption, wherein the at least one energy reflection, shadowing, transmission or absorption detecting sensor is used to identify one or more of the group comprising:
   shape and form of the human or the animal, wherein the at least one energy reflection, shadowing, transmission or absorption detecting sensor includes one or more selected from the group consisting of: at least one imaging sensor, a visible light or short wavelength infrared camera; and at least one radar sensor;
   macro-movement of the human or the animal, wherein the at least one energy reflection, shadowing, transmission or absorption detecting sensor includes a ranging sensor, wherein the ranging sensor is one of: a ranging radar sensor, an ultrasonic sensor, or a laser sensor;
   micro-movement of the human or the animal, wherein the at least one energy reflection, shadowing, transmission or absorption detecting sensor includes a Doppler sensor, wherein the Doppler sensor is one of: a Doppler radar sensor, an ultrasonic sensor, or a laser sensor.

9. The disinfectant system according to claim 1 wherein the chemical sensor comprises at least one chemical detecting sensor for detecting chemical emissions or reactions.

10. The disinfectant system according to claim 9 wherein the at least one chemical detecting sensor is used to identify the presence of the human or the animal, wherein the at least one chemical detecting sensor includes at least one of the group containing: carbon dioxide sensor; humidity sensor; and volatile organic compounds (VOC) sensor.

11. The disinfectant system according to claim 1 wherein the sensing module further includes at least one electric field sensor for detecting local electric field disturbances, wherein the at least one electric field sensor is used to identify electrical properties of the human or the animal and wherein the at least one electric field sensor includes at least one electrode to detect capacitance changes.

12. The disinfectant system according to claim 1 wherein the sensing module further includes at least one physical disturbance sensor for detecting local physical disturbances, wherein the at least one physical disturbance sensor is used to identify local weight changes through contact with the human or the animal, wherein the at least one physical disturbance sensor is a pressure sensor.

13. The disinfectant system according to claim 1 wherein the sensing module further includes at least one active or passive signal detecting sensor for detecting other active or passive signals, wherein the at least one active or passive signal detecting sensor is used to identify a label attached to the human or the animal and the label includes a transponder or beacon.

14. The disinfectant system according to claim 1 wherein the disinfectant operation is an interruptible process.

15. The disinfectant system according to claim 1 wherein the disinfectant module includes at least one micro-biocidal light source, wherein the light source is at least one of the group including: an ultra violet A (UV-A) light source; an ultra violet B (UV-B) light source; and an ultra violet C (UV-C) light source.

16. The disinfectant system according to claim 1 including a dosage control module for monitoring dosage information derived from disinfectant operations during a predefined operation period, wherein the dosage control module recalibrates the disinfectant module to change the disinfectant operation based on the monitored dosage information and wherein the disinfectant operation includes a timing component and an intensity component, and the recalibration includes adjusting one or more of the timing component and the intensity component.

17. The disinfectant system according to claim 16 including a processing module for receiving and integrating data from the sensing module, and communicating with the disinfectant module and dosage control module.

18. A hospital disinfectant method, including:
providing a disinfectant module comprising at least one micro-biocidal chemical source for carrying out a disinfectant operation within an enclosed space when a predefined condition is met;
providing a sensing module including at least two sensors operable to sense a presence of a human or an animal within the enclosed space when the human or the animal is substantially still and covered under bedding, wherein the at least two sensors comprise a chemical sensor and a micro-movement sensor operable to detect micro-movements of a human or an animal when substantially still and covered under bedding; and
automatically performing a disinfectant operation within the enclosed space when the predefined condition is met, wherein the predefined condition is the absence of the human or the animal within the enclosed space.

19. A sensing system operable to sense a presence of a human or an animal within an enclosed space when the human or the animal is substantially still and covered under bedding, the system being operatively associated with a hospital disinfectant process using at least one micro-biocidal chemical source for carrying out a disinfectant operation within the enclosed space, the system comprising:
at least two sensors comprising a chemical sensor and a micro-movement sensor operable to detect micro-movements of a human or an animal when substantially still and covered under bedding; and
a disinfectant module comprising at least one micro-biocidal chemical source for carrying out the disinfectant operation when a predefined condition is met, wherein the predefined condition is the absence of the human or the animal within the enclosed space, and wherein the disinfectant operation will be automatically disabled when the system senses the presence of the human or the animal within the enclosed space.

* * * * *